(12) United States Patent
Costa Codina

(10) Patent No.: US 10,507,084 B2
(45) Date of Patent: Dec. 17, 2019

(54) DENTAL PROSTHESIS SYSTEM

(71) Applicant: DENTISEL, S.L., Les Franqueses Del Valles (ES)

(72) Inventor: Xavier Costa Codina, Les Franqueses Del Valles (ES)

(73) Assignee: CLINICA DENTAL COSTA CODINA, S.L., Granollers (Barcelona) (ES)

( * ) Notice: Subject to any disclaimer, the term of this patent is extended or adjusted under 35 U.S.C. 154(b) by 13 days.

(21) Appl. No.: 14/399,695

(22) PCT Filed: Apr. 24, 2013

(86) PCT No.: PCT/ES2013/070263
§ 371 (c)(1),
(2) Date: Nov. 7, 2014

(87) PCT Pub. No.: WO2013/167775
PCT Pub. Date: Nov. 14, 2013

(65) Prior Publication Data
US 2015/0147721 A1 May 28, 2015

(30) Foreign Application Priority Data
May 9, 2012 (ES) .................................. 201230695

(51) Int. Cl.
*A61C 8/00* (2006.01)
*A61C 13/265* (2006.01)

(52) U.S. Cl.
CPC ............ *A61C 8/0016* (2013.01); *A61C 8/005* (2013.01); *A61C 8/0037* (2013.01);
(Continued)

(58) Field of Classification Search
CPC ... A61C 13/2656; A61C 8/0016; A61C 8/005; A61C 8/0048; A61C 8/0068; A61C 8/0037; A61C 8/006; A61C 8/0001
See application file for complete search history.

(56) References Cited

U.S. PATENT DOCUMENTS 4,850,870 A * 7/1989 Lazzara ............... A61C 8/0048
433/173
5,125,840 A * 6/1992 Durr ..................... A61C 8/005
433/173
(Continued)

FOREIGN PATENT DOCUMENTS

DE        39 12 364        6/1990
DE    10 2009 015358 A1    9/2010
(Continued)

OTHER PUBLICATIONS

International Search Report dated Sep. 13, 2013 issued in corresponding International patent application No. PCT/ES2013/070263.
(Continued)

*Primary Examiner* — Cris L. Rodriguez
*Assistant Examiner* — Hao D Mai
(74) *Attorney, Agent, or Firm* — Ostrolenk Faber LLP

(57) ABSTRACT

A flexible dental prosthesis system including: a longitudinally elongated flexible screw having a first end suitable for being fitted by means of threading in a dental implant and a second open end that can be inwardly deformed having a threaded hole on its inside and a projecting flange on its outside; a transmucosal post with a through hole suitable for inserting the flexible screw; and an upper connection element having a hole at one of its ends suitable for being coupled on the second end of the flexible screw by means of (Continued)

an inner recess in said hole corresponding with the projecting flange on the outside of the second end of the flexible screw.

12 Claims, 5 Drawing Sheets

(52) U.S. Cl.
CPC .......... *A61C 8/0048* (2013.01); *A61C 8/0068* (2013.01); *A61C 13/2656* (2013.01); *A61C 8/0001* (2013.01); *A61C 8/006* (2013.01)

(56) References Cited

U.S. PATENT DOCUMENTS

| | | | | |
|---|---|---|---|---|
| 5,129,388 | A * | 7/1992 | Vignaud | A61B 17/7004 411/385 |
| 5,145,371 | A * | 9/1992 | Jorneus | A61C 8/005 433/173 |
| 5,368,483 | A * | 11/1994 | Sutter | A61C 8/0022 433/173 |
| 5,536,268 | A * | 7/1996 | Griss | A61B 17/7023 606/254 |
| 5,816,812 | A * | 10/1998 | Kownacki | A61C 8/0022 433/174 |
| 5,882,200 | A * | 3/1999 | Sutter | A61C 8/0001 433/173 |
| 5,882,350 | A * | 3/1999 | Ralph | A61B 17/70 606/278 |
| 5,904,483 | A | 5/1999 | Wade | |
| 6,068,479 | A | 5/2000 | Kwan | |
| 6,159,008 | A | 12/2000 | Kumar | 433/163 |
| 6,159,010 | A * | 12/2000 | Rogers | A61C 8/0048 433/172 |
| 6,168,436 | B1 * | 1/2001 | O'Brien | A61C 8/005 433/172 |
| 6,168,439 | B1 * | 1/2001 | Anderson | A63F 3/0423 273/299 |
| 6,227,859 | B1 * | 5/2001 | Sutter | A61C 8/005 433/173 |
| 6,431,866 | B2 * | 8/2002 | Hurson | 433/172 |
| 6,986,660 | B2 * | 1/2006 | Kumar | A61C 8/005 433/173 |
| 7,014,464 | B2 * | 3/2006 | Niznick | A61C 8/0001 433/173 |
| 8,272,871 | B2 * | 9/2012 | Hurson | A61C 8/0001 433/173 |
| 8,651,858 | B2 * | 2/2014 | Berckmans, III | A61C 1/084 433/24 |
| 8,944,818 | B2 * | 2/2015 | Robb | A61C 8/008 433/172 |
| 9,326,832 | B2 * | 5/2016 | Zuker | A61C 8/005 |
| 2001/0023350 | A1 * | 9/2001 | Choi | A61B 17/7032 606/264 |
| 2003/0224331 | A1 | 12/2003 | Kumar et al. | |
| 2004/0180308 | A1 * | 9/2004 | Ebi | A61C 8/0001 433/173 |
| 2004/0243126 | A1 * | 12/2004 | Carbone | A61B 17/7034 606/279 |
| 2005/0154391 | A1 * | 7/2005 | Doherty | A61B 17/7038 606/278 |
| 2007/0073291 | A1 * | 3/2007 | Cordaro | A61B 17/7032 606/86 A |
| 2007/0099153 | A1 * | 5/2007 | Fromovich | A61C 8/0022 433/174 |
| 2010/0055645 | A1 * | 3/2010 | Mullaly | A61C 8/0025 433/174 |
| 2011/0129798 | A1 * | 6/2011 | Zucker | A61C 8/005 433/173 |
| 2012/0059426 | A1 * | 3/2012 | Jackson | A61B 17/7008 606/300 |
| 2013/0096636 | A1 * | 4/2013 | Courtney | A61B 17/7037 606/308 |
| 2014/0011155 | A1 * | 1/2014 | Thomsen | A61C 8/0001 433/29 |

FOREIGN PATENT DOCUMENTS

| | | |
|---|---|---|
| EP | 1 362 560 A1 | 11/2003 |
| WO | WO 02/24104 A1 | 3/2002 |

OTHER PUBLICATIONS

Chinese Office Action issued in Chinese Patent Application No. 201380028522.6 dated Aug. 29, 2016 with an English language translation.

* cited by examiner

DENTAL PROSTHESIS SYSTEM

CROSS REFERENCE TO RELATED APPLICATIONS

The present application is a 35 U.S.C. § 371 National Phase conversion of PCT/ES2013/070263, filed Apr. 24, 2013, which claims benefit of Spanish application no. P201230695, filed May 9, 2012 the disclosure of which is incorporated herein by reference. The PCT International Application was published in the Spanish language.

OBJECT OF THE INVENTION

The present invention relates to the field of dental implants, and more specifically to a dental prosthesis system which allows coupling various elements on the dental implant without having to resort to using screws.

BACKGROUND OF THE INVENTION

The use of dental implants and prostheses in the field of dentistry for replacing lost teeth or teeth that must be extracted for any reason is extremely widespread. Generally, dental prosthesis implantation process is performed in several phases including, first, a minor surgical procedure for inserting the implant in bone. In general, a waiting time of a few months must then be provided to allow the gum to heal and cover the implant, while osseointegration, i.e., the integration of dental implant inside the patient's bone, occurs at the same time. Next, the upper part of the implanted dental implant must be accessed to place a healing post, such that the gum can heal around same. Finally, models of the patient's set of teeth will be taken with which a suitable dental prosthesis that can be installed in said dental implant will be made.

The phases described in the preceding paragraph require inserting various elements in and extracting them from the installed dental implant, each of them with specific functions (healing post, transfer elements for preparing molds of the dental piece, posts for coupling the prosthesis, etc.). All these elements are coupled by means of screwing the elements in and unscrewing them from the already installed dental implant, which can be a very laborious method for the specialist as well as being unpleasant and uncomfortable for the patient.

Therefore, there is a need in the art of a system which allows coupling various elements on a dental implant in a simpler and quicker manner compared to the systems known to date in the field of dentistry.

DESCRIPTION OF THE INVENTION

Therefore, to solve the technical problem considered above, the present invention discloses a flexible dental prosthesis system which allows coupling various elements on a dental implant of the type conventionally known in the art. The system of the present invention is characterized by comprising:
  a longitudinally elongated flexible screw having a first end and a second end. The first end is suitable for being fitted by means of threading in a dental implant, whereas the second end is flexible, open and can be inwardly deformed, and has a threaded hole on its inside and a projecting flange on its outside;
  a transmucosal post having a through hole in which said flexible screw is inserted; and
  an upper connection element having a hole at one of its ends suitable for being coupled on the second end of the flexible screw by means of an inner recess in said hole corresponding with the projecting flange on the outside of the second end of the flexible screw.

Therefore, according to the invention, the upper connection element is coupled on the second end of the flexible screw by means of a "click" type connection. In fact, upon coupling the upper connection element on the flexible screw, the second end of said flexible screw will deform inwardly, allowing its insertion in the hole of the upper connection element. When the projecting flange of the flexible screw reaches the corresponding inner recess of the upper connection element, the second end of the flexible screw will recover its original shape, both elements thus being coupled to one another.

DESCRIPTION OF THE DRAWINGS

The present invention will be better understood in reference to the following drawings illustrating the preferred embodiments of the invention, provided by way of example and which must not be interpreted as limiting the invention in any manner.

PREFERRED EMBODIMENT OF THE INVENTION

Figure 1:
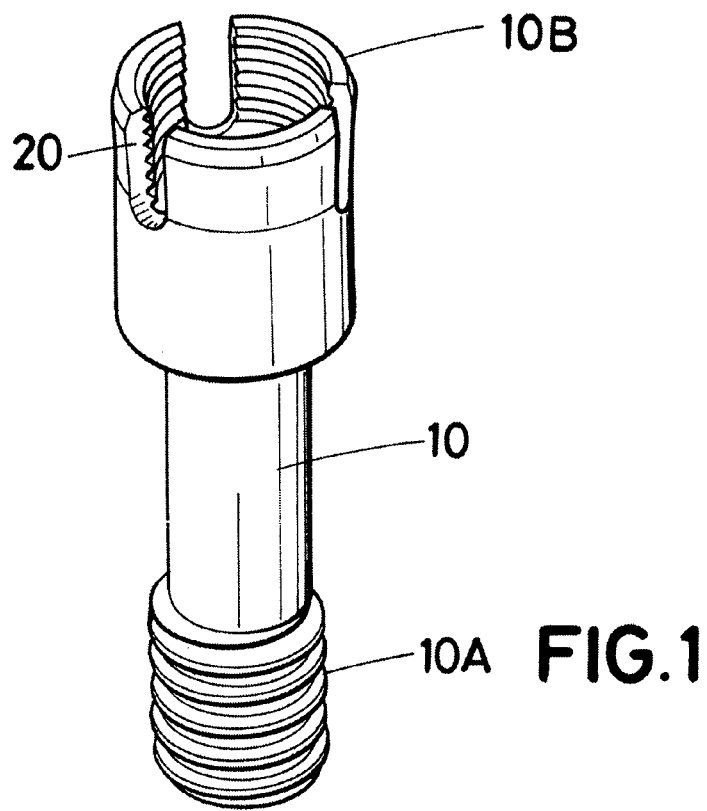
FIG. 1 shows a perspective view of a flexible screw according to the preferred embodiment of the present invention.

Each of the various elements comprised in the dental prosthesis system according to the present invention will be described separately below. First, the system comprises a flexible screw (10), shown in FIG. 1. The function of said flexible screw (10) is, on one hand, to fix the transmucosal post (12) to a dental implant (14) already installed in the patient, and on the other hand, to assure the attachment with the various upper connection elements (16) that must be coupled thereto in the various phases of the method. Said attachment with the corresponding upper connection element (16) is made in two ways: by means of conventional threading as already known in the prior art, and by means of a "click" type connection as will be described below in this document.

Returning to FIG. 1, it can be seen that the flexible screw (10) has a longitudinally elongated shape with two ends (10A, 10B). The first end (10A) is suitable for being fitted by means of threading in a dental implant (14) as will be described below in this document. The second end (10B) is flexible, open and can be inwardly deformed. This second end (10B) has a threaded hole on its inside and a projecting flange (18) on its outside. Furthermore, it can be seen that in this preferred embodiment of the present invention, said second flexible end (10B) of said flexible screw (10) has three grooves (20) extending in the longitudinal direction of said flexible screw (10). These grooves (20) facilitate the inward bending of said second flexible end (10B) upon coupling an upper connection element (16) thereon.

Figure 2:
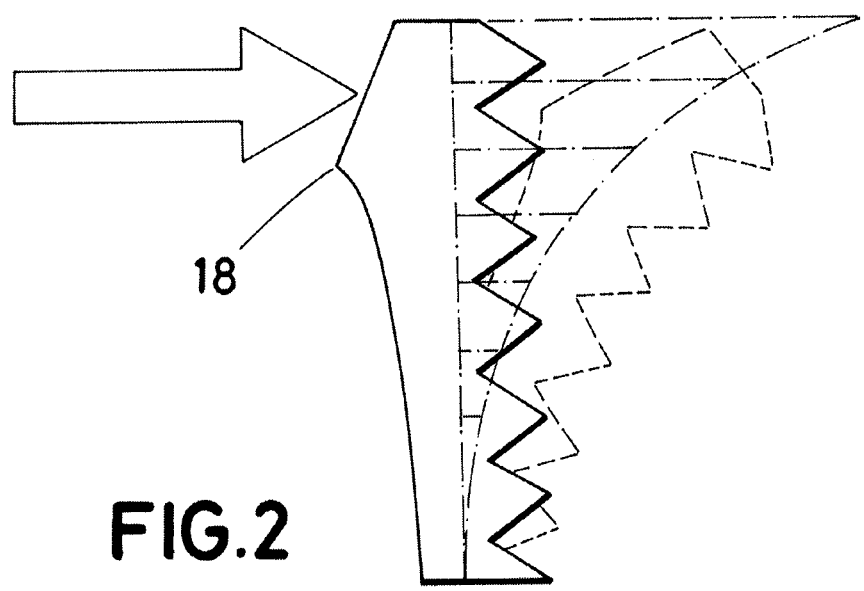
FIG. 2 shows a longitudinal section view of the second end of the flexible screw of FIG. 1.
Figure 3:
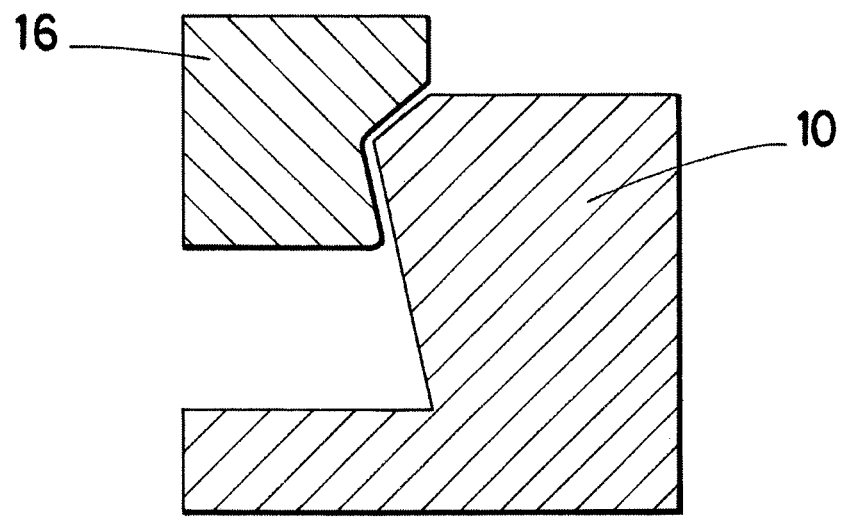
FIG. 3 shows a schematic longitudinal section view of the coupling between the second flexible end of the flexible screw and an upper connection element according to the preferred embodiment of the present invention.

FIG. 2 shows in a clearer and exaggerated manner said inward bending of the second flexible end (10B). In the resting state, the second flexible end (10B) is in the vertical position shown in said drawing. Upon inserting an upper connection element (16) from the top, said second flexible end (10B) bends inwards (in the direction of the arrow as shown in FIG. 2) towards the inclined position shown in said drawing. Once the inner recess of the upper connection element (16) reaches the projecting flange (18) of the second flexible end (10B), the latter recovers its initial vertical position and the "click" type connection takes place between both elements (schematically shown in FIG. 3).

It must be pointed out that, according to the preferred embodiment of the present invention, and given that the flexible screw (10) must be able to be inserted in an already existing dental implant (14), the design of the first end (10A) thereof may vary depending on the dental implant (14) in which it must be inserted. In turn, the second flexible end (10B) is intended for being connected only to other elements of the system according to the present invention, and therefore the design thereof may be a common design in all cases.

Figure 4:
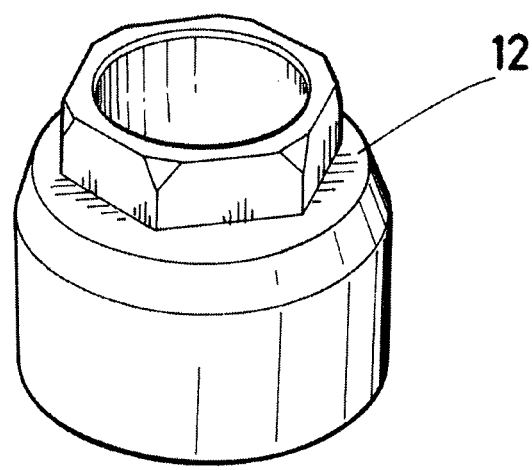
FIG. 4 shows a perspective view of a transmucosal post according to the preferred embodiment of the present invention.

Now referring to FIG. 4, it shows a transmucosal post (12) according to the preferred embodiment of the present invention. Like in the preceding case, the persons skilled in the art will understand that given that said transmucosal post (12) must be adapted to an already existing dental implant (14), its design will vary depending on the design of the dental implant (14). This transmucosal post (12) has a through hole on which the flexible screw (10) shown above is inserted, such that the post supports and surrounds the screw, protecting it from lateral stresses. This transmucosal post (12) will also be used as a base and support for the various upper connection elements (16) that must be installed.

Figure 5:
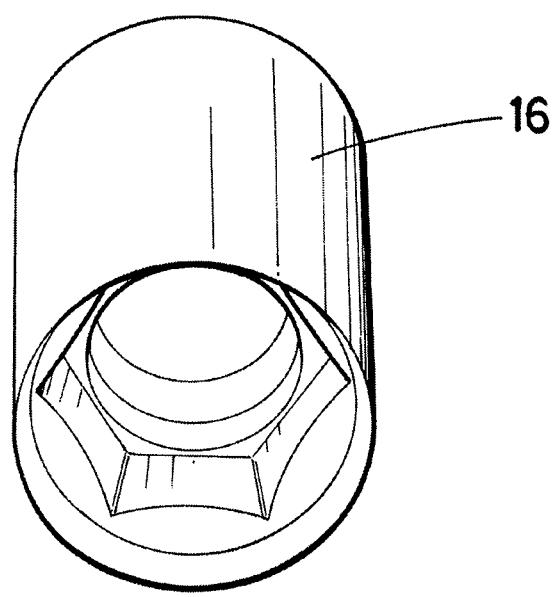
FIG. 5 shows a perspective view of the part for attaching to a flexible screw of an upper connection element according to the preferred embodiment of the present invention.

The upper connection element (16) according to the preferred embodiment of the present invention can be of various types, such as for example, a temporary post, an interface, an impression transfer element, etc. FIG. 5 shows in a perspective view the part of an upper connection element (16) of this type which will be used for coupling to a flexible screw (10) and transmucosal post (12) as described above. The upper connection element (16) has a hole at the end shown in FIG. 5 which will be coupled on the second end (10B) of the flexible screw (10) as a result of an inner recess in said hole as described above, not shown in this drawing. Said inner recess corresponds with the projecting flange (18) of the second end (10B) of the flexible screw (10).

The upper connection element (16) also has an inner hexagonal profile suitable for being coupled with an outer hexagonal profile of a transmucosal post (12) such as shown in FIG. 4. The rotation of the upper connection element (16) with respect to said transmucosal post (12) is thus blocked. In some cases, the upper connection element (16) will also have a through hole, such that after coupling on the flexible screw (10) by means of said inner recess and corresponding projecting flange (18), it allows fixing said coupling by means of inserting a screw through the upper connection element (16) and threading it in the inner threaded hole of the flexible screw (10).

According to another embodiment of the present invention, the upper vertices of said hexagonal end of the transmucosal post (12) intended for being coupled with the upper connection element (16) have a conical shape. The possibility of blocking or unblocking the rotation of the upper connection element (16) is thus provided depending on whether the inner profile of said upper connection element (16) is hexagonal (preceding embodiment) or conical. When making bridges of more than one tooth, the upper connection element (16) is preferably unblocked.

Figure 6:
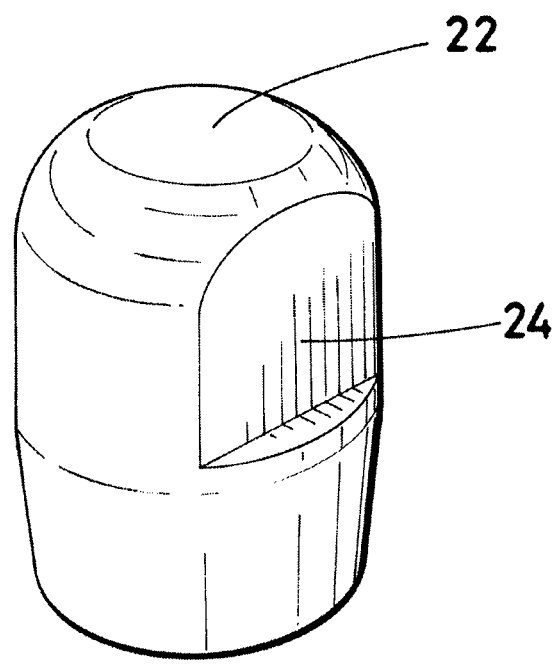
FIG. 6 shows a perspective view of an alginate impression transfer element according to the preferred embodiment of the present invention.

Now referring to FIG. 6, it shows an alginate impression transfer element (22) according to the preferred embodiment of the present invention. Said element (22) is used for taking dental impressions with alginate as known by the persons skilled in the art. Although not seen in this drawing, the part of the element (22) that will be connected to the flexible screw (10) will clearly have the design described in the preceding FIG. 5. Said element (22) also has two sets of planar faces (24) (of which only one is shown in FIG. 5) which, after being analyzed with a dental scanner, will allow determining the exact position of the transmucosal post (12) in a three-dimensional virtual space by means of geometric correlation.

Figure 7:
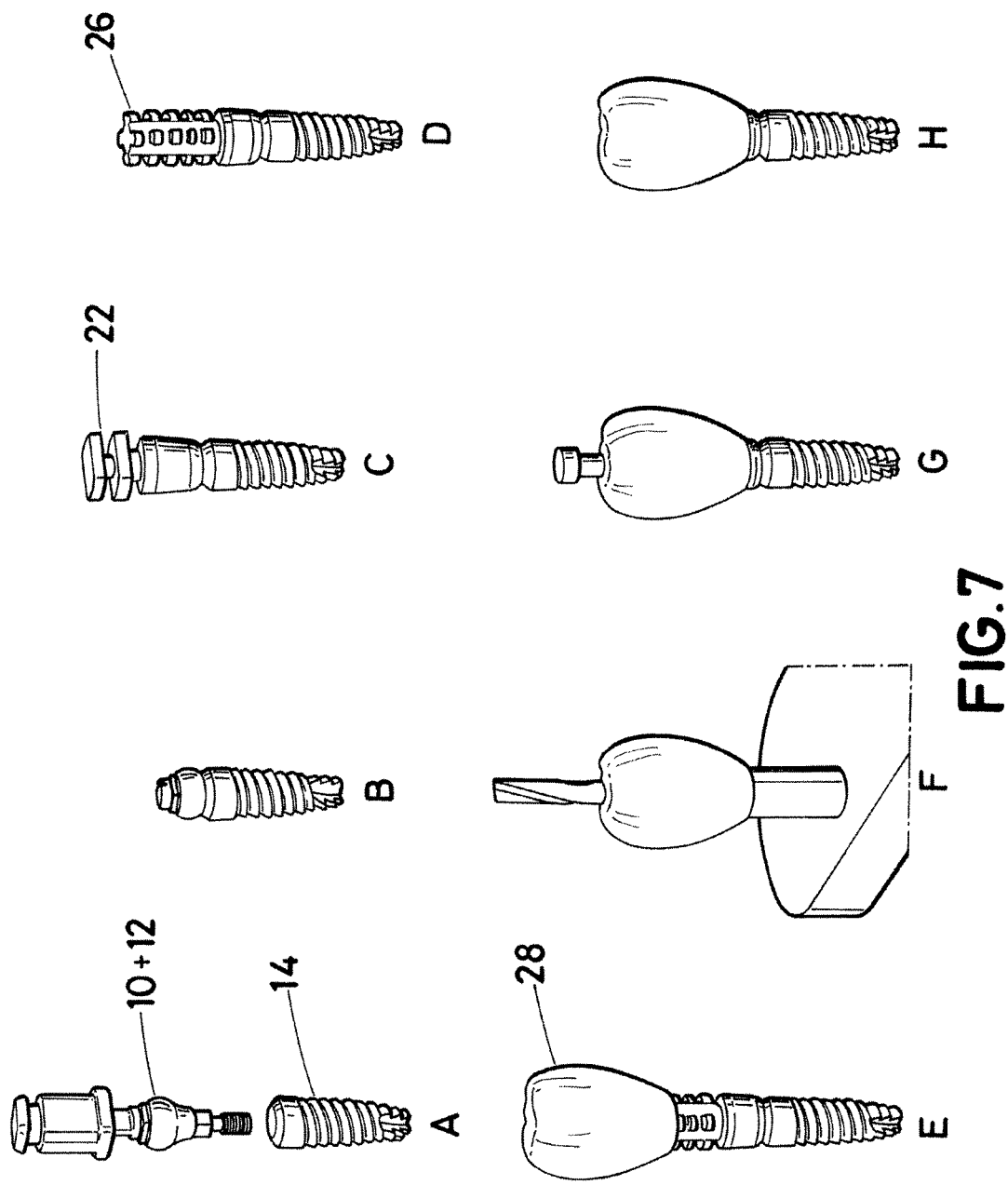
FIG. 7 shows a sequence of the dental prosthesis implantation phases using the system according to the preferred embodiment of the present invention.
Figure 8:
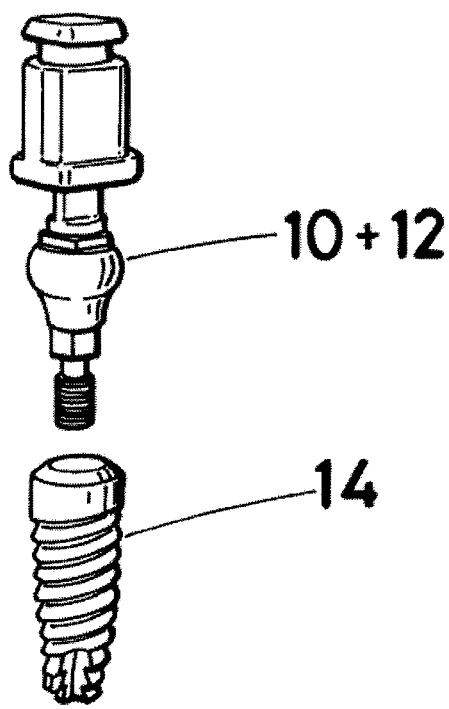
FIG. 8 shows a flexible screw and transmucosal post integrated to form a single part.

Finally in relation to FIG. 7, it shows a series of images (A-H) schematically illustrating various phases during the installation of a dental prosthesis using the dental prosthesis system according to the present invention. In phase A, the flexible screw (10)-transmucosal post (12) assembly is inserted by means of threading in a dental implant (14) already installed in a patient. In phase B, said flexible screw (10)-transmucosal post (12) assembly already installed and stabilized in the dental implant (14) can be seen. In phase C, an impression transfer element (22) is seen coupled on the second end (10B) of the flexible screw (10), which will be used for taking measurements and making a dental prosthesis mold for that specific patient. Subsequently, in phase D, another upper connection element (16) is seen coupled on the flexible screw (10), in this case a temporary post (26). A temporary prosthesis (28) is made on said temporary post (phase E). In phase F, how a precision drilling is subsequently performed on the upper part of said prosthesis (28) can be seen, thus allowing the access to a through hole on the inside of said temporary post (26). Fitting and screwing (phase G) are performed to provide a more secured hold (phase G) of the temporary prosthesis (28), which is now suitably secured to the flexible screw (10) and therefore the dental implant (14).

The various elements comprised in the dental prosthesis system of the present invention can be made of any suitable material. Both the flexible screw and the transmucosal post are preferably made of commercial titanium grade V, since in the case of the flexible screw, titanium has the mechanical properties suitable for bending to enable using the mechanical spring, maintaining enough rigidity to support the screw that fixes the upper connection element. In turn, in the case of the transmucosal post, titanium has optimal mechanical properties and further allows integrating the transmucosal post in the tissues surrounding the implant. Titanium does not cause allergic reactions or rejections in the body, which is important in this case since the transmucosal post can contact the bone and the soft connective tissue.

In turn, the material used for making the upper connection element will depend on the specific element. For example, in the case of a temporary post or an interface, it can be made of a material selected from the group consisting of titanium and PEEK, whereas if it is an impression transfer element, it will preferably be made of POM.

Although the present invention has been described in reference to several preferred embodiments thereof, the persons skilled in the art will readily understand that variations and modifications can be applied to the preceding description without departing from the scope and spirit of the present invention. For example, although it has been described that the second end of the flexible screw comprises three longitudinal grooves, other embodiments thereof may not comprise grooves, or may comprise grooves in different number or other deigns which also facilitate the inward bending of said second end of the flexible screw.

The coupling between the upper connection element and the second end of the flexible screw is preferably reversible, i.e., said upper connection element can be removed from said flexible screw.

Furthermore, although the flexible screw and the transmucosal post have been described as independent elements in the preceding description, according to another preferred embodiment of the present invention, said flexible screw and said transmucosal post are made integral with one another forming a single part known as a flexible post.

The invention claimed is:

1. Dental prosthesis system, comprising:
   a longitudinally elongated flexible screw having a first end that includes threading configured to be received in a dental implant and a second open flexible end that can be bent inwardly by inwardly bending and having a threaded hole with threads inside of said second open flexible end and a projecting flange outside of said second open flexible end;
   a transmucosal post positioned between the first end and the second flexible end of the longitudinally elongated flexible screw; and
   an upper connection element having a hole at one of its ends, the upper connection element being configured to be click-coupled by click-coupling on the second open flexible end of the flexible screw by means of an inner recess in said hole corresponding with the projecting flange outside of the second open flexible end of the flexible screw,
   wherein the coupling between the upper connection element and the second open flexible end of the flexible screw is reversible, whereby said upper connection element is decoupled from said flexible screw,
   wherein the second open flexible end of said flexible screw has a plurality of longitudinal grooves to facilitate the inwardly bending of said second open flexible end upon coupling the upper connection element and the second open flexible end,
   wherein said second open flexible end of the flexible screw has only three of said plurality of longitudinal grooves, and
   wherein the second open flexible end of the flexible screw recovers its original shape when the projecting flange reaches the corresponding inner recess of the upper connection element.

2. Dental prosthesis system according to claim 1, wherein the upper connection element is selected from the group consisting of an impression transfer element, a temporary post and an interface.

3. Dental prosthesis system according to claim 1, wherein the upper connection element comprises a through hole such that after coupling on the flexible screw by means of said inner recess and corresponding projecting flange, the through hole allows fixing of said coupling by means of inserting a screw through the upper connection element and threading the screw in the inner threaded hole of the flexible screw.

4. Dental prosthesis system according to claim 1, wherein said flexible screw and said transmucosal post are made integral with one another forming a single part.

5. Dental prosthesis system according to claim 1, wherein the transmucosal post has, at its end intended for being coupled with the upper connection element, an outer polygonal profile, thus blocking rotation of the upper connection element with a corresponding inner profile coupled thereon.

6. Dental prosthesis system according to claim 5, wherein the outer profile of the end of the transmucosal post intended for being coupled with the upper connection element is hexagonal.

7. Dental prosthesis system according to claim 6, wherein upper vertices of the hexagonal end of the transmucosal post intended for being coupled with the upper connection element have a conical shape.

8. Dental prosthesis system according to claim 1, wherein the flexible screw and the transmucosal post are made of commercial titanium grade V.

9. Dental prosthesis system according to claim 1, wherein the upper connection element is made of a material selected from the group consisting of titanium and PEEK if said upper connection element is a temporary post or an interface, and is made of POM if said upper connection element is an impression transfer element.

10. Dental prosthesis system according to claim 1, wherein the transmucosal post has a through hole in which the flexible screw is inserted.

11. Dental prosthesis system according to claim 1, wherein said plurality of longitudinal grooves are equidistant.

12. Dental prosthesis system according to claim 1, further comprising a dental implant configured to receive the threading of the first end.

* * * * *